(12) United States Patent
Bayach

(10) Patent No.: US 11,890,367 B1
(45) Date of Patent: Feb. 6, 2024

(54) ANTI-AGING COMPOSITION BASED ON MIXED ESTER OF STILBENIC EXTRACT

(71) Applicant: KING FAISAL UNIVERSITY, Al-Ahsa (SA)

(72) Inventor: Imene Bayach, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/130,478

(22) Filed: Apr. 4, 2023

(51) Int. Cl.
*A61K 8/67* (2006.01)
*A61Q 19/08* (2006.01)
*A61K 8/49* (2006.01)

(52) U.S. Cl.
CPC ............ *A61K 8/678* (2013.01); *A61K 8/4973* (2013.01); *A61Q 19/08* (2013.01); *A61K 2800/805* (2013.01)

(58) Field of Classification Search
None
See application file for complete search history.

(56) References Cited

U.S. PATENT DOCUMENTS

| | | |
|---|---|---|
| 2007/0148109 A1 | 6/2007 | Panin |
| 2012/0171308 A1 | 7/2012 | Da Luz Moreira et al. |
| 2014/0315995 A1 | 10/2014 | Dreher |

FOREIGN PATENT DOCUMENTS

| | | |
|---|---|---|
| AU | 2015387145 B2 | 9/2016 |
| CA | 2796315 A1 | 10/2011 |
| WO | 2016146144 A1 | 9/2016 |
| WO | 2022173524 A2 | 8/2022 |

OTHER PUBLICATIONS

Nam et al., "Design and Synthesis of π-Extended Resveratrol Analogues and In Vitro Antioxidant and Anti-Inflammatory Activity Evaluation", Molecules, Feb. 2021; 26(3): 646.
Bayach et al., "Oligostilbenoids from the Heartwood of N. Heimii: Role of Non-Covalent Association in their Biogenesis", Chemistry: An Asian Journal, vol. 10, No. 1, pp. 198-211 (Jan. 2015).

*Primary Examiner* — Nicole P Babson
(74) *Attorney, Agent, or Firm* — Nath, Goldberg & Meyer; Richard C. Litman

(57) ABSTRACT

A cosmetic composition having an anti-aging effect, and particularly cosmetic compositions comprising natural polyphenols, such as oligostilbenes. The polyphenols are stabilized by forming mixed polyphenol-vitamin E esters. These esters may be hydrolyzed by esterases of the skin, when topically applied, to regenerate the active ingredients in their native state and thereby treat and/or reduce skin aging or other skin diseases or deteriorations.

20 Claims, 2 Drawing Sheets

ANTI-AGING COMPOSITION BASED ON MIXED ESTER OF STILBENIC EXTRACT

BACKGROUND

1. Field

The disclosure of the present patent application relates to a cosmetic composition having an anti-aging effect, and particularly to cosmetic compositions comprising natural polyphenols, such as oligostilbenes.

2. Description of the Related Art

Human skin is a complex organ (the largest human organ) which extends over the entire body. As the outermost organ, the skin forms a protective barrier to protect the body from harm. Skin is subject to abuse from both external and internal factors, which can result in skin aging. Skin aging occurs in two ways: (1) chronological aging (i.e., the natural aging process) and (2) through UV rays in sunlight, which accelerate the natural aging process (i.e., photoaging). Chronological aging may result in thinning, loss of elasticity, and/or general degradation of the skin. By contrast, photoaging, which is most acute in areas of habitual sun exposure, may result in changes such as elastosis, atrophy, wrinkling, vascular changes (i.e., diffuse erythema, ecchymosis, and telangiectasias), pigmentary changes (i.e., lentigines, freckles, and areas of hypo- and hyper-pigmentation), and/or the development of seborrheic keratosis, actinic keratosis, comedones, and cysts.

While the skin is equipped with natural defenses that help to protect it from damage, these defenses can become overwhelmed, which can lead to skin damage.

Skin appearance and elasticity is a widespread cosmetic concern. In addition, in recent years, skin protection has also become a great health concern.

Antioxidants are commonly used to improve the therapeutic or cosmetic performance of dermatological and cosmetic formulations. However, in order to be effective, antioxidants must remain in their unoxidized form. As a result, maintenance of antioxidant stability in a formulation suitable for topical administration has often proven to be a challenge.

Natural polyphenols, such as oligostilbenes, are known to have potent antioxidant activity. However, these polyphenolic compounds have the disadvantage of being very oxidizable, which makes their inclusion in topical formulations for skin treatment difficult if not impossible.

Due to the ongoing demand for anti-skin aging treatments, there is a significant need in the art for a new way to effectively formulate these antioxidants into stable topical compositions. Thus, a stabilized antioxidant solving the aforementioned problems is desired.

SUMMARY

The present subject matter relates to cosmetic compositions having an anti-aging effect. These compositions are obtained by derivatizing an oligostilbenic extract rich in polyphenols by the formation of stable, mixed polyphenol vitamin E esters. That is, the polyphenols and/or oligostilbenes are coupled to vitamin E (α-tocopherol) to prevent their oxidation and cause the polyphenols to be more stable, in use. The formed esters may possibly be hydrolyzed by the esterases of the skin, thus regenerating the active ingredients in their native state. The esterification of these compounds stabilizes them and thus facilitates their formulation into a topical cosmetic composition, such as a cosmetic cream.

In an embodiment, the present subject matter relates to a mixed diester of oligostilbene with vitamin E having the formula:

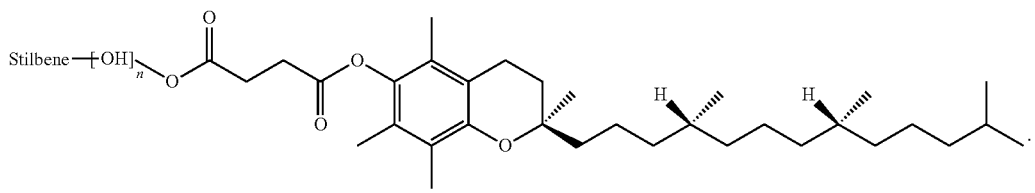

In another embodiment, the present subject matter relates to a process for coupling a polyphenol to vitamin E, the process comprising: esterifying vitamin E with a diacid anhydride to obtain a vitamin E diacid ester; chlorinating the vitamin E diacid ester with a chloride reagent to obtain a vitamin E acyl chloride; dissolving an extract of the polyphenol and 4-Dimethylaminopyridine (DMAP) in pyridine to obtain a polyphenol solution; and adding the vitamin E acyl chloride to the polyphenol solution to obtain a coupled polyphenol-vitamin E product.

In a further embodiment, the present subject matter relates to a topical composition comprising the mixed diester of oligostilbene with vitamin E described herein and a cosmetically acceptable carrier. Also contemplated is a method for reducing skin aging of a patient, as well as a method for treating skin diseases of a patient generally, comprising topically administering the topical compositions described herein to a patient in need thereof.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
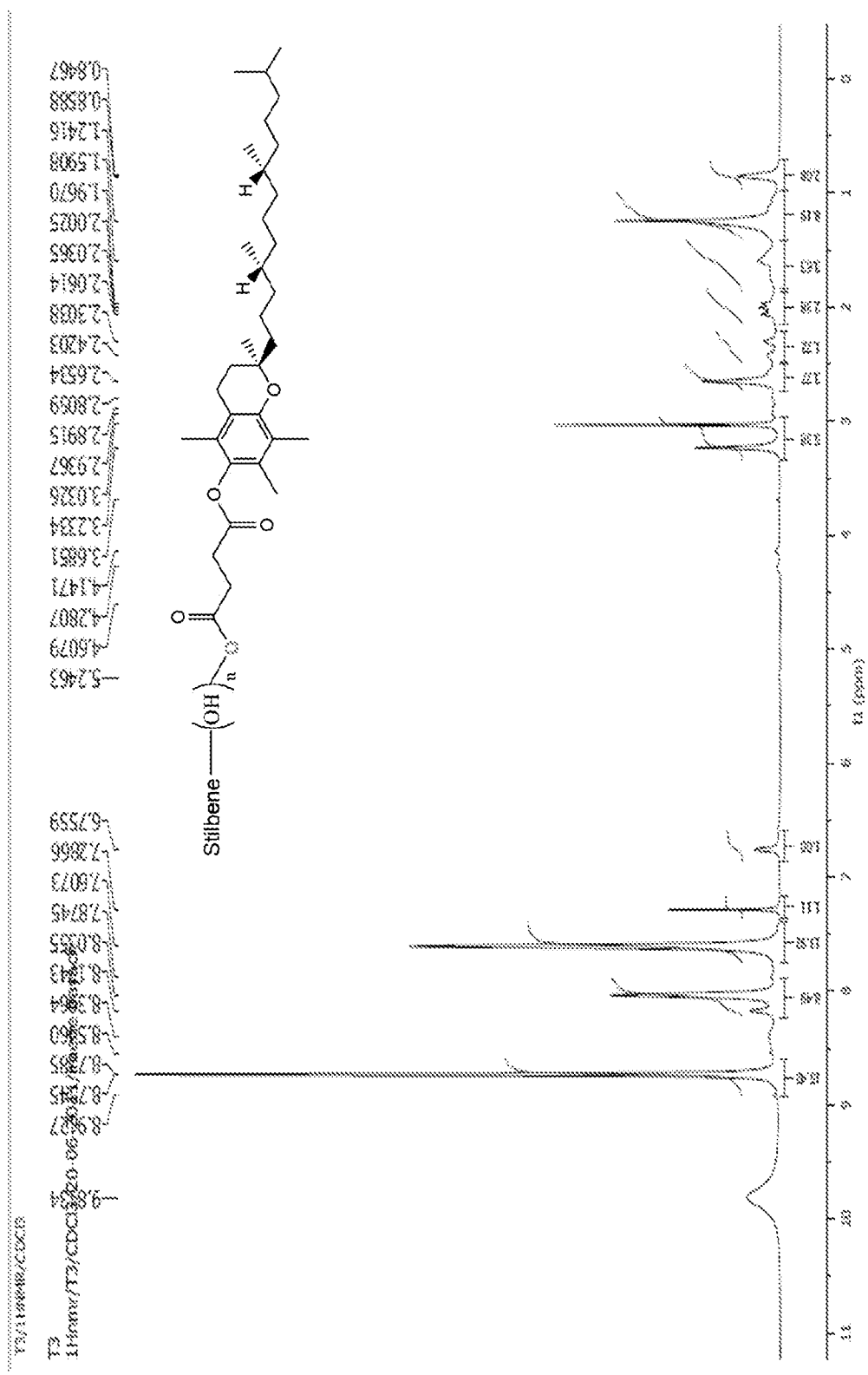
FIG. 1 shows the 1H NMR spectrum of the synthesized ester of oligostilbene/vitamin E.
Figure 2:
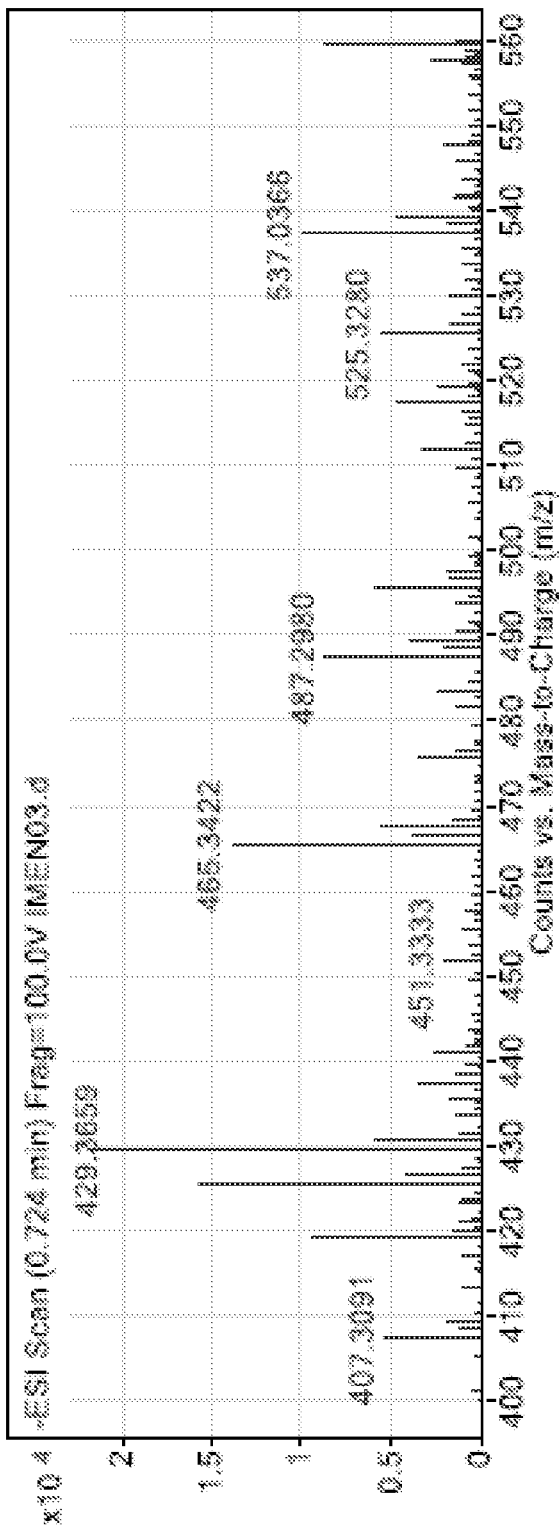
FIG. 2 shows the MS spectrum of the vitamin E succinyl acyl chloride intermediate.

The following definitions are provided for the purpose of understanding the present subject matter and for construing the appended patent claims.

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically infeasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

A "cosmetic composition," as used herein, include without limitation, personal care product, skin product, skin cream, skin gel, skin ointment, skin lotion, skin serum, anti-aging product, skin rejuvenation product, skin conditioner, moisturizer, feminine product, hygiene product, skin patch, skin mask, tissue wipe, lipstick, mascara, rouge, foundation, blush, eyeliner, lip liner, lip gloss, lip balm, facial or body powder, sunscreens, sunblocks, nail polish, mousse, sprays, styling gels, nail conditioner, bath and shower gels, shampoos, conditioners, cream rinses, hair sprays, hair dyes and coloring products, soaps, body scrubs, exfoliants, astringents, depilatories and permanent waving solutions, antidandruff formulations, anti-sweat and antiperspirant compositions, shaving, preshaving and after shaving products, leave-on conditioners, deodorants, cold creams, deodorants, cleansers, rinses, vulvar product, vaginal product, or the like; whether in the form of creams, lotions, gels, ointments, macro-emulsions, micro-emulsions, nano-emulsions, serums, balms, colloids, solutions, liquids, suspensions, dispersions, compacts, solids, powders, pencils, spray-on formulations, brush-on formulations, patches, iontophoretic patches, microprojection patches, microneedle patches, skin delivery enhancing systems, bandage, tissue cloths, wipes, masks, aerosols, pastes, soap bars, cosmetic devices, and/or any other forms readily known to those skilled in the art.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to cosmetic compositions having an anti-aging effect. These compositions are obtained by derivatizing an oligostilbenic extract rich in polyphenols by the formation of stable, mixed polyphenol vitamin E esters. These esters may possibly be hydrolyzed by the esterases of the skin, thus regenerating the active ingredients in their native state. The esterification of these compounds stabilizes them and thus facilitates their formulation into a topical cosmetic composition, such as a cosmetic cream.

Various aspects now will be described more fully hereinafter. Such aspects may, however, be embodied in many different forms and should not be construed as limited to the embodiments set forth herein. Rather, these embodiments are provided so that this disclosure will be thorough and complete, and will fully convey its scope to those skilled in the art.

In an embodiment, the present subject matter relates to a mixed diester of oligostilbene with vitamin E having the formula:

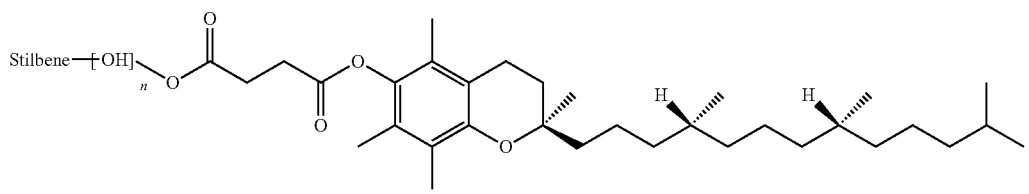

The present subject matter is directed to derivatizing an oligostilbenic extract by attaching a vitamin E unit to 1 or 2 OH of each oligostilbene via a dicarboxylic group. Accordingly, in an embodiment, the present subject matter relates to a process for coupling a polyphenol to vitamin E, the process comprising: esterifying vitamin E (α-tocopherol) with a diacid anhydride, such as, by way of non-limiting example, succinic anhydride to obtain a vitamin E diacid ester, such as, by way of non-limiting example, vitamin E succinyl ester; chlorinating the vitamin E diacid ester with a chlorine containing reagent to obtain a vitamin E diacid chloride, such as, by way of non-limiting example, vitamin E succinyl chloride; dissolving an extract of the polyphenol and 4-Dimethylaminopyridine (DMAP) in a solvent such as, by way of non-limiting example, pyridine to obtain a polyphenol solution; and adding the vitamin E diacid chloride to the polyphenol solution to obtain a coupled polyphenol-vitamin E product.

In one embodiment in this regard, the polyphenol can be an oligostilbene and the coupled polyphenol-vitamin E product can be a mixed diester of oligostilbene with vitamin E. In this regard, the chemical structures of oligostilbenes are well known, and the methods described herein could be applicable to couple other polyphenols to vitamin E. However, oligostilbenes specifically are polyphenols derived mainly from resveratrol (3,5,12-trihydroxystilbene) by oxidative phenolic coupling between the olefinic group of one unit and an aromatic ring of another. The oligostilbenes which are currently known include mainly dimers, trimers and tetramers. The oligostilbenoids discussed herein can be isolated from the heartwood of *Neobalanocarpus heimi* according to the discussion in https://doi.org/10.1002/asia.201402673, the contents of which are hereby incorporated by reference in their entirety. The heartwood extract composition can contain one or more of the oligostilbenes discussed therein.

By way of non-limiting example, the mixed diester of oligostilbene with vitamin E produced by the present methods can include one or more of the above oligostilbenes, and can have the general formula:

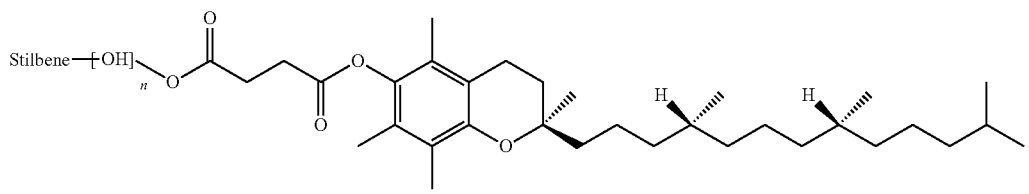

In one embodiment, the present synthetic processes use a diacid anhydride, such as succinic anhydride, which is selected based on the reactivity of the anhydride and the intrinsic toxicity of the free diacid. Accordingly, the esterification step of the present processes uses vitamin E+a base+the anhydride to lead to the formation of the ester of vitamin E with a free COOH group, which is further susceptible to chlorination with a chloride reagent. The use of the anhydride instead of an acid makes it possible to carry out the reaction without forming any co-products, which eliminates any reprocessing steps and facilitates the analysis of the formed esters. The reaction mechanism of this reaction corresponds to a nucleophilic substitution on the carbonyl function of the anhydride by the OH group, which leads to an ester, per the below general scheme:

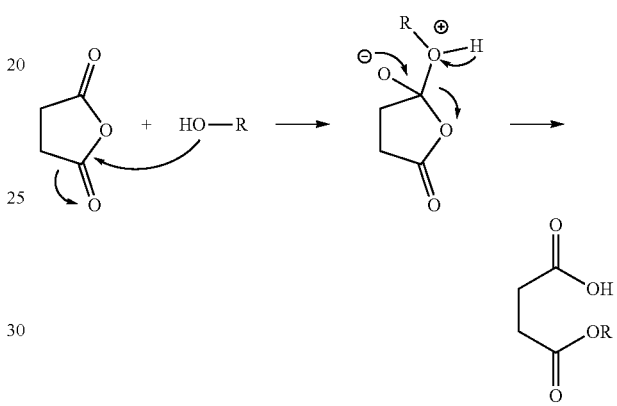

In an embodiment, the esterifying step can comprise dissolving the vitamin E and a catalyst in a solvent at a temperature just below the solvent's boiling point to obtain a vitamin E solution; and adding the succinic anhydride to the vitamin E solution. In this regard, the solvent used in the esterification step can be selected from the group consisting of pyridine, DMF, THF, and combinations thereof. In one embodiment, the solvent can be pyridine. Similarly, the catalyst used in the esterification step can be a base selected from the group consisting of $Et_3N$, NaH, $(CH_3)_3COK$, DMAP, and combinations thereof. In one embodiment, the base can be DMAP. In another embodiment, the vitamin E and the succinic anhydride can be present and reacted in an about 1:1 molar ratio.

As noted, in an embodiment, after the esterifying step is completed, the resultant ester of vitamin E with a free COOH group, i.e., the vitamin E diacid ester, can be chlorinated in a chlorinating step with a chloride reagent. In this regard, the chloride reagent, by way of non-limiting example, can be any of $PCl_3$, $PCl_5$, $CO_2Cl_2$, or $SOCl_2$. One useful chloride reagent in this regard is thionyl chloride, a.k.a. sulfur chloride dioxide ($SOCl_2$). Thionyl chloride, or sulfur dichloride oxide ($SOCl_2$), is a liquid at room temperature and reacts with carboxylic acids to form acyl chloride, sulfur dioxide and hydrogen chloride, as per the below general scheme:

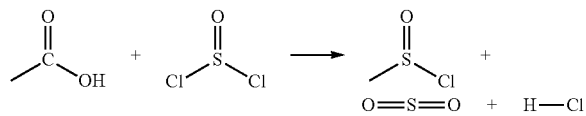

The separation of the products of this reaction is simplified, as both side-products are gaseous. The elimination of any sulfur dichloride excess from the Vitamin E diacid chloride formed, such as, by way of non-limiting example, Vitamin E succinyl chloride, can be carried out, for example, in a rotary evaporator connected by a pipe to the outside when the reaction mixture is dried.

The chlorinating step can be conducted at ambient temperature and can involve using about 5.5 mmoles of the vitamin E diacid ester per about 1 equivalent of the chloride reagent.

As noted, an extract of the polyphenol, such as an oligostilbene, and a base can be separately dissolved in a solvent to obtain a polyphenol solution. In some embodiments, the base and/or the solvent in this polyphenol dissolution can be the same as those used in the esterification step mentioned above; in other embodiments, the base and/or the solvent can be different from those used in the esterification step mentioned above. By way of non-limiting example, the solvent used in the polyphenol dissolution can be selected from the group consisting of pyridine, DMF, THF, and combinations thereof. In one embodiment, the solvent can be pyridine. Similarly, the base used in the polyphenol dissolution can be a base selected from the group consisting of $Et_3N$, NaH, $(CH_3)_3COK$, DMAP, and combinations thereof. In one embodiment, the base can be DMAP.

In an embodiment, the polyphenol and the base can be dissolved in the solvent at a temperature of about 90° C.

Lastly, the vitamin E diacid chloride can be added to the polyphenol solution to obtain a coupled polyphenol-vitamin E product. In this regard, the vitamin E diacid chloride, such as, by way of non-limiting example, vitamin E succinyl chloride, can be reacted in the presence of the base with the dissolved polyphenol extract, or dissolved oligostilbene extract, to obtain the coupled polyphenol, or oligostilbene-vitamin E product. This reaction can occur using a stoichiometry such that only 1 or 2 α-tocopherols are fixed per oligostilbene, by way of non-limiting example, a density of 5 OHs for each 456 g of material (corresponding to a dimer). So, 1 equivalent per 456 g of material will fix one α-tocopherol per dimer. Tetramers will include 2 tocotrienols, trimers 1 or 2.

Since acid chlorides are among the most reactive derivatives of carboxylic acids, as an acylating agent, they react with alcohols to form an ester and a hydrogen chloride molecule as depicted in the general reaction scheme below:

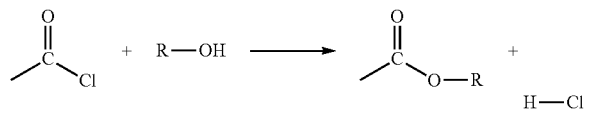

Accordingly, in an embodiment the polyphenol and the vitamin E diacid chloride can be combined in a molar ratio of about 4.5:13.

In a further embodiment, the present subject matter relates to a topical composition comprising the mixed diester of oligostilbene with vitamin E as described herein and a cosmetically acceptable carrier.

Non-limiting examples of suitable cosmetically acceptable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

In employing the present compositions, any cosmetically acceptable excipients for topical administration, including solid, semi-solid, liquid or aerosol dosage forms, such as, for example, liquids, suspensions, creams, gels, ointments, lotions, aerosols, or the like. In an embodiment, the topical composition can be a cosmetic cream.

Any of the compositions described herein can also be included in kits. Such kits contain, in one or more containers, these compositions as well as instructions for use.

In another embodiment, the present subject matter relates to a method for reducing skin aging of a patient, comprising topically administering the topical composition as described herein to a patient in need thereof. In this regard, after the topical composition is administered to the patient, the mixed diester of oligostilbene with vitamin E can be hydrolyzed by esterases of the skin. In an embodiment, the skin aging can be photo-induced skin aging.

Also provided herein are methods for modifying free radical damage to skin by administering any of the present compositions to a patient in an amount sufficient to treat and/or prevent free radical damage to skin.

The present subject matter also provides methods of treating, alleviating, improving and/or ameliorating a symptom, condition, disorder, or disease (e.g., of the skin) associated with free radicals, the method comprising administering an effective amount of any of the present compositions to a patient in need thereof. For example, the symptom, condition, disorder, or disease associated with free radicals is selected from the group consisting of sun induced skin damage, skin aging, inflammatory skin diseases or disorders, degenerative skin diseases or disorders, and/or cancer (e.g., skin cancer). Diseases and disorders of skin that also may result from radical damage include, but are not limited to skin cancer, skin irritation or inflammation, dermatitis, allergy, psoriasis, acne, eczema, and rosacea. In addition, diseases and disorders of skin may result from radical damage caused by visible light exposure, UV-radiation exposure, IR-radiation exposure, X-ray radiation exposure, smoking, air pollution, nutritional deficit or imbalance, and certain medications causing free radicals.

In any of the methods described herein, treating, alleviating, improving and/or ameliorating the symptom can neutralize free radicals. These methods may involve the repeated topical administration of the composition to the individual (e.g., the patient). For example, any of the present compositions can be administered to the patient at least once or twice a day for at least 30 days or more.

Also provided are methods for modifying free radical damage to skin by administering an effective amount of any of the present compositions to the skin of a patient. In such methods, the effective amount is sufficient to treat, prevent, improve, treat and prevent, treat and improve, prevent and treat, prevent and improve, and/or treat and prevent and improve or otherwise modify free radical damage to the skin.

All terms such as "skin aging", "signs of skin aging", "topical application", and the like are used in the sense in which they are generally and widely used in the art of developing, testing and marketing cosmetic and personal care products.

Skin aging is classified into intrinsic aging and extrinsic aging depending on its cause. Intrinsic aging is a process by which the skin structure and the physiological functions of the skin deteriorate regardless of environmental changes as a human gets older. Extrinsic aging is caused by continuous exposure to external environment such as sunlight and air pollutants. Especially, skin aging caused by sun light is called photoaging. Ultraviolet (UV) light from the sun is the main cause of the physiological and morphological changes in aged skin.

Continuous exposure to the sun is the main cause of extrinsic aging of skin. The UV component of sunlight, particularly UVA and UVB, is generally believed to be the principal causative agent in this process called photoaging. The extent of UV exposure required to cause "photoaging" is not currently known, although the amount sufficient to cause erythema (reddening, commonly described as sunburn) in human skin is quantified as the "minimal erythema dose" (MED) from a given UV light source. Repeated exposure to sunlight UV at levels that cause erythema and tanning are, nevertheless, commonly associated with photoaging.

There is a difference between the physiology of intrinsically-aged (i.e., chronologically-aged) skin in comparison with that of photoaged skin. Chronologically-aged skin typically maintains a smooth and unblemished appearance, in comparison with the leathery, blotchy, and often deep wrinkling of photoaged skin. Photoaging is characterized clinically by coarseness, wrinkles, mottled pigmentation, sallowness, laxity, telangiectasia, lentigines, purpura and relative ease of bruising, atrophy, depigmented areas, eventually premalignant, and ultimately malignant neoplasm (i.e., abnormal mass of tissue as a result of neoplasia, which is the abnormal proliferation of cells). Photoaging commonly occurs in skin that is generally exposed to sunlight such as the face, ears, bald areas of the scalp, neck, décolleté, forearms, and hands.

"Signs of skin aging" include, but are not limited to, all outward visibly and tactilely perceptible manifestations as well as any other macro or micro effects due to skin aging. Such signs may be induced or caused by intrinsic factors (showing as chronological aged skin) and extrinsic factors (showing as environmental skin damage including but not limited photo-aged skin). These signs may result from processes which include, but are not limited to, the development of textural discontinuities such as wrinkles and coarse deep wrinkles, fine or skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including under eye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

The compositions herein can be applied topically onto any areas of the face, neck, neckline, décolleté, scalp, hand, palm, arm, leg, foot, sole, chest, breast, back, abdomen, buttock, vulva, or penis and scrotum, anus, and/or any other skin areas of the human body.

Furthermore, the compositions herein can also be applied locally or topically to other surfaces of the human body, including hair and nail, or any wound, scar, or skin and mucosal surface areas affected by atrophy, or other conditions, disorders and diseases associated with free radical related skin damage.

In one embodiment, the present treatment methods can improve free radical related skin damage through topical application of an effective amount of the composition as defined above to the skin. More specifically, these methods can be used to treat, alleviate, and/or ameliorate a symptom, condition, disorder, and/or disease associated with free radicals. For example, the symptom, condition, disorder and/or disease may include sun induced skin damages, electromagnetic radiation (visible light, UV, IR) induced skin damages, air pollution induced skin damages, smoking induced skin damages, skin aging, skin inflammatory diseases or disorders, skin degenerative diseases or disorders, nutrition induced skin damages, metabolism induced skin damages, and cancer. The compositions may neutralize free radicals.

Such methods may require the repeated topical administration of the composition. Some benefits can be noticed within a few hours to a few days after topically applying the compositions according to the present invention on the affected human skin or human tissue. However, it takes generally at least 30 days to notice benefits. Thereby, the composition should be applied to the affected human skin or human tissue at least once to twice a day for at least 30 days.

Also provided are methods of modifying free radical damage to skin by administering an effective amount of any of the present compositions to the skin of a patient. Ideally, the effective amount is sufficient to treat, prevent, or treat and prevent free radical damage to the skin.

Determination of an effective dose or amount (e.g., therapeutically, cosmetically, pharmaceutically, and/or medicinally effective dose) of any of the present compositions is within the routine level of skill in the art.

EXAMPLES

Example 1

Esterification Reaction of Vitamin E by Succinic Anhydride

In a 50 ml reactor, equipped with mechanical stirring at 750 rpm, a thermometer, N2 bubbling and topped with a condenser, 6 mmol of alcohol (eugenol: 1 g, α-tocopherol: 2.6 g) and 0.2% of catalyst are dissolved in the solvent at a temperature just below the boiling point of the solvent used (eugenol: 253.5° C., α-tocopherol: 235° C.). Then, 6 mmoles of succinic anhydride (0.6 g) are added. After stirring overnight, the reaction medium is then decanted to be distilled under reduced pressure in order to remove the excess reagent.

The progress of the reaction and the conversion rates are influenced by the molar ratio of the reactants, as well as the nature of the base and solvent. The best yield was given by entry No. 6 as seen in Table 1, the rate of conversion of eugenol, and α-tocopherol into succinyl ester in view of the TLC results seems satisfactory for the continuation of the reaction.

TABLE 1

| Entry | Base | solvent | Boiling point (° C.) |
|---|---|---|---|
| 1 | Et$_3$N | Pyridine | 115.35 |
| 2 | Et$_3$N | DMF | 153 |
| 3 | Et$_3$N | THF | 66 |
| 4 | NaH | THF | 66 |
| 5 | (CH$_3$)$_3$COK | THF | 66 |
| 6 | DMAP | Pyridine | 115.35 |

Example 2

Chlorination Reaction

Succinyl eugenol (test product, compound 1) and vitamin E (products of interest, compound 2) were prepared. Chlorination permits the obtained acid obtained to be converted to the corresponding acyl chloride.

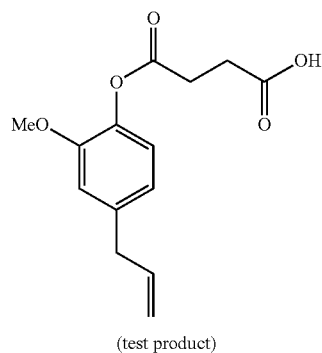

(test product)

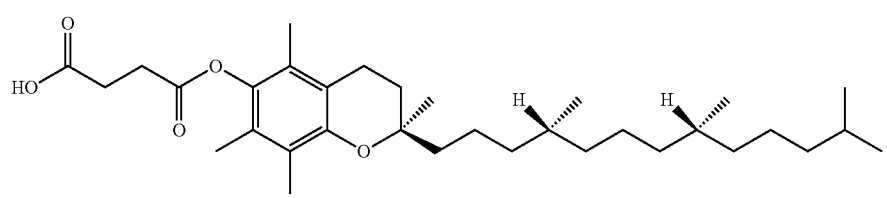

Into a 50 ml three-necked flask surmounted by a condenser, equipped with a separatory funnel, a gas outlet device and a magnetic stirrer, the prepared succinyl ester is introduced, then, carefully and drop by drop, 1 equivalent of the chlorinating agent is added (reaction from eugenol: 4 mmoles, of vitamin E: 5.5 mmoles). The reaction mixture is stirred at 600 rpm and at ambient temperature, for 4 hours. The reaction crude is then evaporated under vacuum.

TLC analysis of products before and after reaction show a slight difference because the polarity of the two compounds are close. Obtention of compound 4 is confirmed by mass spectroscopy.

These chloride compounds are reactive and require special storage conditions. It is preferable to proceed directly to the acylation step.

Example 3

Acylation Reaction

In a 50 ml reactor, equipped with mechanical stirring at 750 rpm and N2 bubbling, 4.5 mmoles of the stilbene extract (1 g) and 0.2% of DMAP are dissolved in pyridine and heated to 90° C. in an oil bath for 6 hours. 13 mmoles of acyl Compound 1

Compound 2 chloride prepared (compounds 3 (test product) and 4) are then added to the reaction mixture. Stirring is continued overnight while maintaining the heating.

The products (compounds 5 (test product) and 6) thus purified were first analyzed by chromatographic methods in order to verify the composition of the reaction medium. The chromatograms revealed the existence in the reaction crudes of new compounds. This was confirmed by the presence of different spots on the TLC plates.

By infrared analysis, an absence of the band characteristic of the vibration of the O—H bonds (3200 cm-1-3600 cm-1) was observed, which means that there is no longer any alcohol function in the structure of the products. In 1H NMR, the synthesis of the diester (compound 6) is proven by the disappearance of the peak corresponding to the hydroxyl.

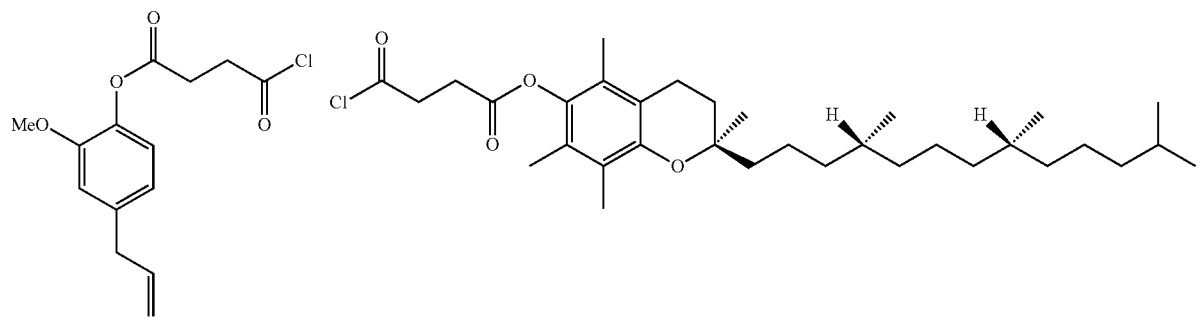

Chemical structures of compound 3 and 4

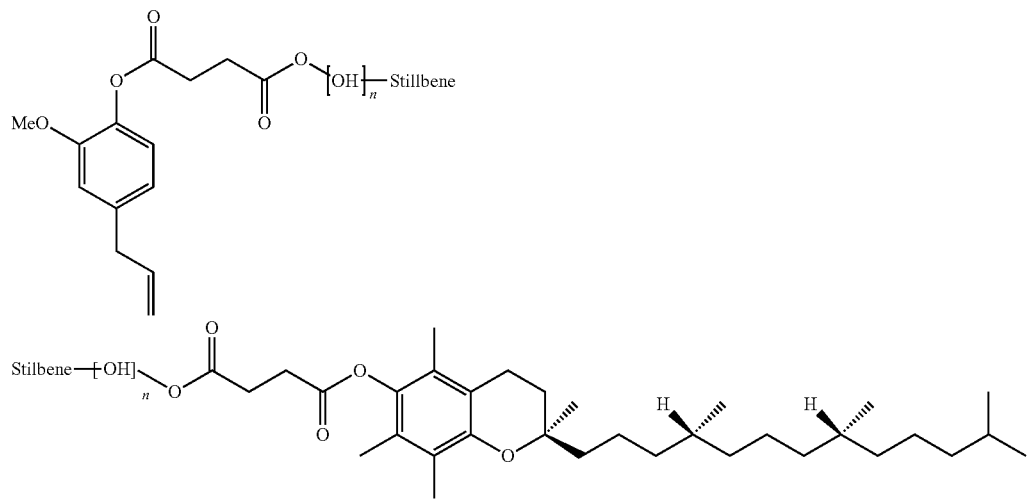

Compound Structures of Compound 5 and 6

It is to be understood that the cosmetic compositions comprising natural polyphenols, such as oligostilbenes, are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A mixed diester of oligostilbene with vitamin E having the formula:

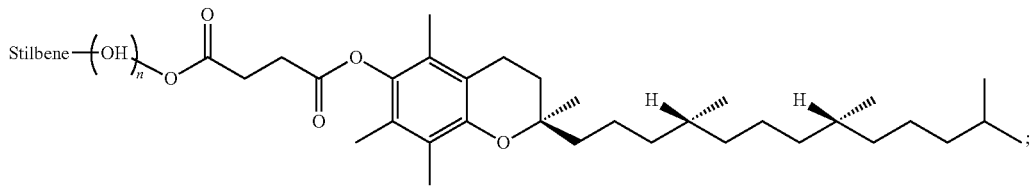

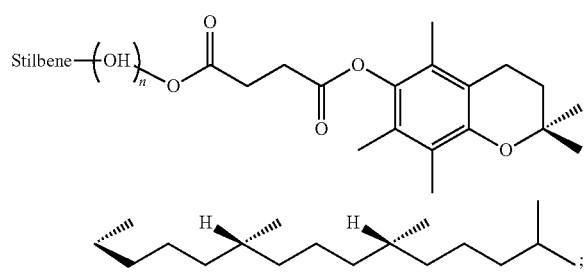

wherein n is 1 or 2.

2. A process for coupling a polyphenol to vitamin E, the process comprising:
esterifying vitamin E with a diacid anhydride to obtain a vitamin E diacid ester;
chlorinating the vitamin E diacid ester with a chloride reagent to obtain a vitamin E diacid chloride;
dissolving an extract of the polyphenol and 4-Dimethylaminopyridine (DMAP) in pyridine to obtain a polyphenol solution; and
adding the vitamin E diacid chloride to the polyphenol solution to obtain a coupled polyphenol-vitamin E product.

3. The process of claim 2, wherein the polyphenol is an oligostilbene and the coupled polyphenol-vitamin E product is a mixed diester of oligostilbene with vitamin E.

4. The process of claim 3, wherein the mixed diester of oligostilbene with vitamin E has the formula:
wherein n is 1 or 2.

5. The process of claim 2, wherein the esterifying step comprises:
dissolving the vitamin E and a catalyst in a solvent at a temperature below the solvent's boiling point to obtain a vitamin E solution; and
adding the diacid anhydride to the vitamin E solution.

6. The process of claim 5, wherein the solvent is selected from the group consisting of pyridine, DMF, THF, and combinations thereof.

7. The process of claim 6, wherein the solvent is pyridine.

8. The process of claim 5, wherein the catalyst is a base selected from the group consisting of $Et_3N$, NaH, $(CH_3)_3COK$, DMAP, and combinations thereof.

9. The process of claim 8, wherein the base is DMAP.

10. The process of claim 9, wherein the diacid anhydride is succinic anhydride, the vitamin E diacid ester is vitamin E succinyl ester, and the vitamin E diacid chloride is vitamin E succinyl acyl chloride.

11. The process of claim 10, wherein the vitamin E and the succinic anhydride are present in an about 1:1 molar ratio.

12. The process of claim 2, wherein the chloride reagent is thionyl chloride ($SOCl_2$).

13. The process of claim 2, wherein the chlorinating step is conducted at ambient temperature and comprises combining about 5.5 mmoles of the vitamin E diacid ester per about 1 equivalent of the chloride reagent.

14. The process of claim 2, wherein the polyphenol and the 4-Dimethylaminopyridine (DMAP) are dissolved in the pyridine at about 90° C.

15. The process of claim 2, wherein the extract of the polyphenol is an oligostilbenic mixture obtained from *Neobalanocarpus heimi*.

16. A topical composition comprising the mixed diester of oligostilbene with vitamin E of claim 1 and a cosmetically acceptable carrier.

17. The topical composition of claim 15, wherein the composition is a cosmetic cream.

18. A method for reducing skin aging of a patient, comprising topically administering the topical composition of claim 15 to a patient in need thereof.

19. The method of claim 17, wherein, after the topical composition is administered to the patient, the mixed diester of oligostilbene with vitamin E are hydrolyzed by esterases of the skin.

20. The method of claim 17, wherein the skin aging is photo-induced skin aging.

\* \* \* \* \*